United States Patent [19]

Yasuo

[11] Patent Number: 5,171,429
[45] Date of Patent: Dec. 15, 1992

[54] APPARATUS FOR DISCHARGING WATER WITH PASSAGE SELECTION SENSOR

[75] Inventor: Takashi Yasuo, Tokoname, Japan

[73] Assignee: Inax Corporation, Tokoname, Japan

[21] Appl. No.: 700,160

[22] PCT Filed: Sep. 21, 1990

[86] PCT No.: PCT/JP90/01212
§ 371 Date: Jun. 24, 1991
§ 102(e) Date: Jun. 24, 1991

[87] PCT Pub. No.: WO91/05114
PCT Pub. Date: Apr. 18, 1991

[30] Foreign Application Priority Data

Sep. 29, 1989 [JP] Japan .................................. 1-254481
Sep. 29, 1989 [JP] Japan .................................. 1-254482

[51] Int. Cl.⁵ .............................................. B01D 35/14
[52] U.S. Cl. ........................................ 210/94; 137/551;
137/555; 116/202; 210/96.1; 210/433.1;
362/32; 362/800
[58] Field of Search ............... 137/551, 553, 555, 557,
137/559; 210/85, 94, 96.1, 418, 433.1, 449;
362/32, 276, 800; 116/202, 216, 264; 358/901

[56] References Cited

U.S. PATENT DOCUMENTS

| 4,849,098 | 7/1989 | Wilcock et al. | 210/85 |
| 4,851,818 | 7/1989 | Brown et al. | 210/85 |
| 4,901,207 | 2/1990 | Sato et al. | 362/32 |
| 4,933,080 | 6/1990 | Rundzaitis et al. | 210/420 |
| 5,114,570 | 5/1992 | Nelson et al. | 210/94 |

FOREIGN PATENT DOCUMENTS

| 63-58373 | 7/1988 | Japan | 137/551 |
| 1165936 | 6/1989 | Japan | 210/85 |

Primary Examiner—Robert A. Dawson
Assistant Examiner—Joseph Drodge
Attorney, Agent, or Firm—Kanesaka and Takeuchi

[57] ABSTRACT

The present invention provides an apparatus for discharging water wherein light is emitted to the output water so as to visually identify kinds of water and like. The apparatus includes sensors (9, 29, 134) for sensing characteristics of water, such as the temperature, flow, pressure, pH and hardness of water, passages as selected by a passage selection valve, or integrated flow of water flowing through a filtering element, a light emitting device (7, 31, 150) such as LED for emitting light to the passage or region downstream of the passage in response to the characteristics as sensed, and an optical fiber (11, 12, 36, 37, 152).

14 Claims, 13 Drawing Sheets

APPARATUS FOR DISCHARGING WATER WITH PASSAGE SELECTION SENSOR

TECHNICAL FIELD

The present invention relates to an apparatus for discharging water such as a water faucet and in particular, to an apparatus constructed to emit light to output water in response to the temperature, quality, pressure or volume of water.

BACKGROUND ART

There has been proposed an automatic faucet wherein a switch is operable to change the volume or temperature of the output water. A lamp is turned on and off so that a user may visually recognize the volume or temperature of water.

It is well known that a water purifier includes a purifying agent such as an activated carbon to purify tap water. The water purifier typically includes a changeover valve operable to selectively discharge tap water and purified water. A lamp is turned on when the changeover valve is operated to provide purified water. A sensor (for example, conductance meter) is provided to detect the quality of purified water, and a warning lamp is turned on when the quality of the purified water deteriorates. A similar warning lamp is turned on when the volume of water flowing through the purifying agent exceeds a predetermined level.

Those lamps are often placed in a control box which is separated from a water faucet. In some case, the lamps are mounted to a faucet, but to the upper portion of the faucet, so that water hardly splashes the lamps. A disadvantage with this arrangement is that the user can not easily view the lamps.

DISCLOSURE OF THE INVENTION

According to one aspect of the invention, there is provided an apparatus for discharging water comprising a water passageway, wherein the apparatus further includes sensor means for sensing characteristics of water flowing through the water passageway, and light emitting means for emitting light to the water passageway or a region downstream of the water passageway in response to the characteristics as sensed.

In the apparatus of the present invention, the characteristics includes one or more of the following: water temperature, water flow, water pressure and water concentration.

In the apparatus of the present invention, the water concentration is pH and/or hardness.

According to another aspect of the invention, there is provided an apparatus for discharging water including an outlet port, a plurality of feed water passages connected to the outlet port, and passage selection means for selectively communicating the outlet port with either one of the plurality of feed water passages, wherein the apparatus further includes sensor means for sensing which one of the plurality of feed water passages is selected by the passage selection means, and light emitting means for emitting light to the feed water passage or a region through which water flows from the outlet port in response to the sensing by the sensor means.

In this case, a filtering element is disposed in either one of the feed water passages.

According to a further aspect of the invention, there is provided an apparatus for discharging water including a filtering element, wherein the apparatus further includes sensor means disposed downstream of the filtering element for sensing the quality of water, and light emitting means for emitting light to a passage in the apparatus or a region through which the water flows from an outlet port in response to the sensing by the sensor means.

According to a still further aspect of the invention, there is provided an apparatus for discharging water including a filtering element, wherein the apparatus further includes sensor means for sensing integrated flow of water flowing through the filtering element, and light emitting means for emitting light to a passage in the apparatus or a region through which the water flows from an outlet port in response to the total amount of flow as sensed.

In the apparatus of the present invention, the light emitting means comprises a light emitting device and an optical fiber for guiding light from the light emitting device. Of course, any light emitting device other than LED and any light transmitter other than the optical fiber may be used.

In the present invention, in order to sense a selected one of the passages in the apparatus, a sensor or switch may be used to sense angular position of a handle or valve of the present apparatus. Also, in the present invention, a motor or solenoid is used to change passages, and an electric switch is used to select a desired passage. In such a case, light may be emitted in response to a signal from the electric switch.

In the apparatus of the present invention, since color light is emitted to the output water, the user may view the water as if it is colored. The user almost always views the output water when the water faucet is in use. As such, the user can visually identify water volume or temperature.

According to the present invention, light is emitted to the output water in response to the temperature, flow rate, pressure, pH (hydrogen ion concentration), and hardness of water.

According to another aspect of the invention, light is emitted to water in response to integrated flow of water flowing through the filtering element.

In the present invention, in order to sense a selected one of the passages in the apparatus, a sensor or switch may be used to sense angular position of a handle or valve of the present apparatus. Also, in the present invention, a motor or solenoid is used to change passages, and an electric switch is used to select a desired passage. In such a case, light may be emitted in response to a signal from the electric switch.

In the present invention, the color of output light may be varied in response to the temperature, volume, pressure, pH or hardness of the output water. For example, blue light is emitted when the output water has a temperature of lower than 20°. Red light is emitted when the output water has a temperature of higher than 40°.

BEST MODE FOR CARRYING OUT THE INVENITON

Figure 1:
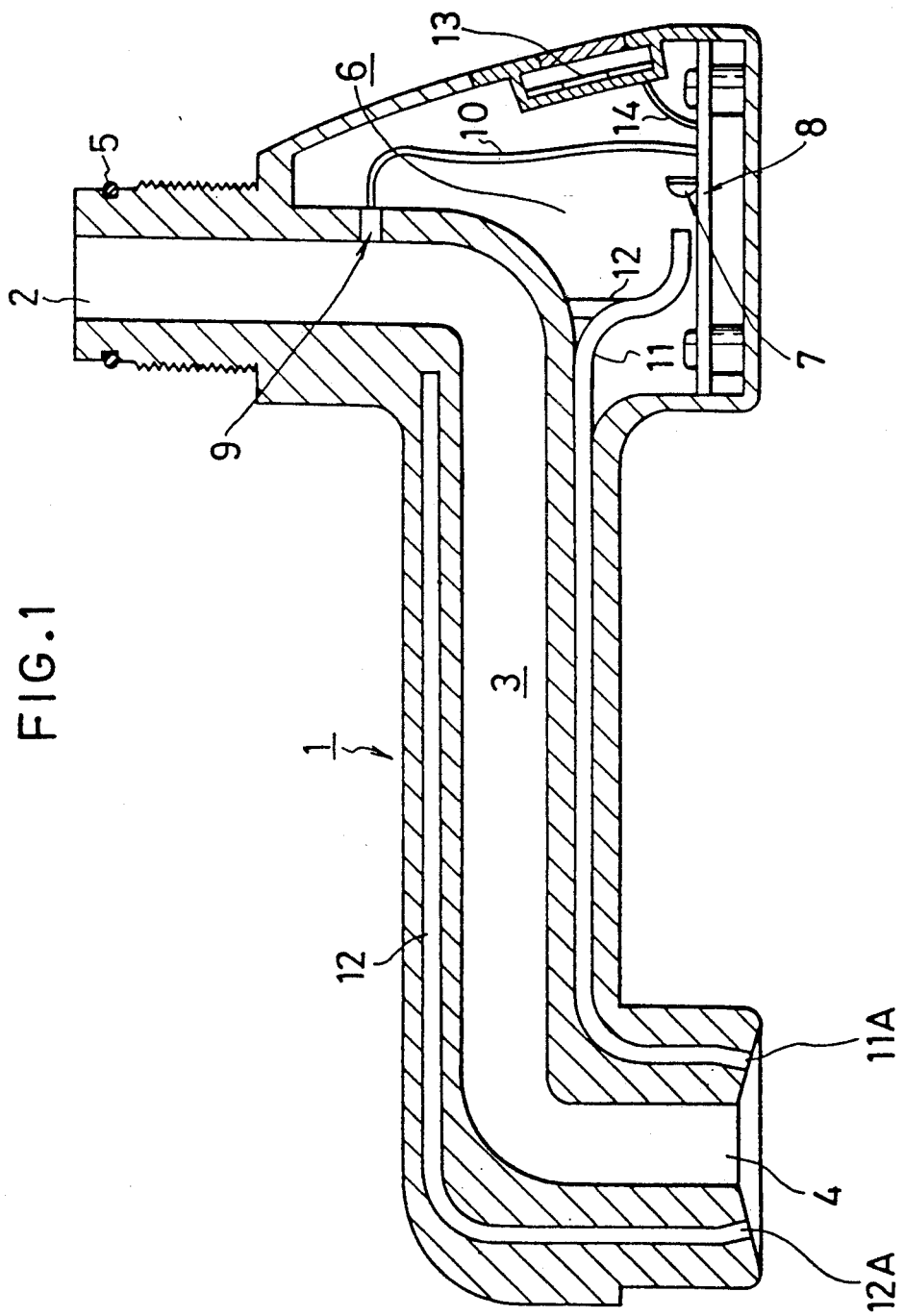
FIG. 1 is a sectional view of one embodiment.
Figure 2:
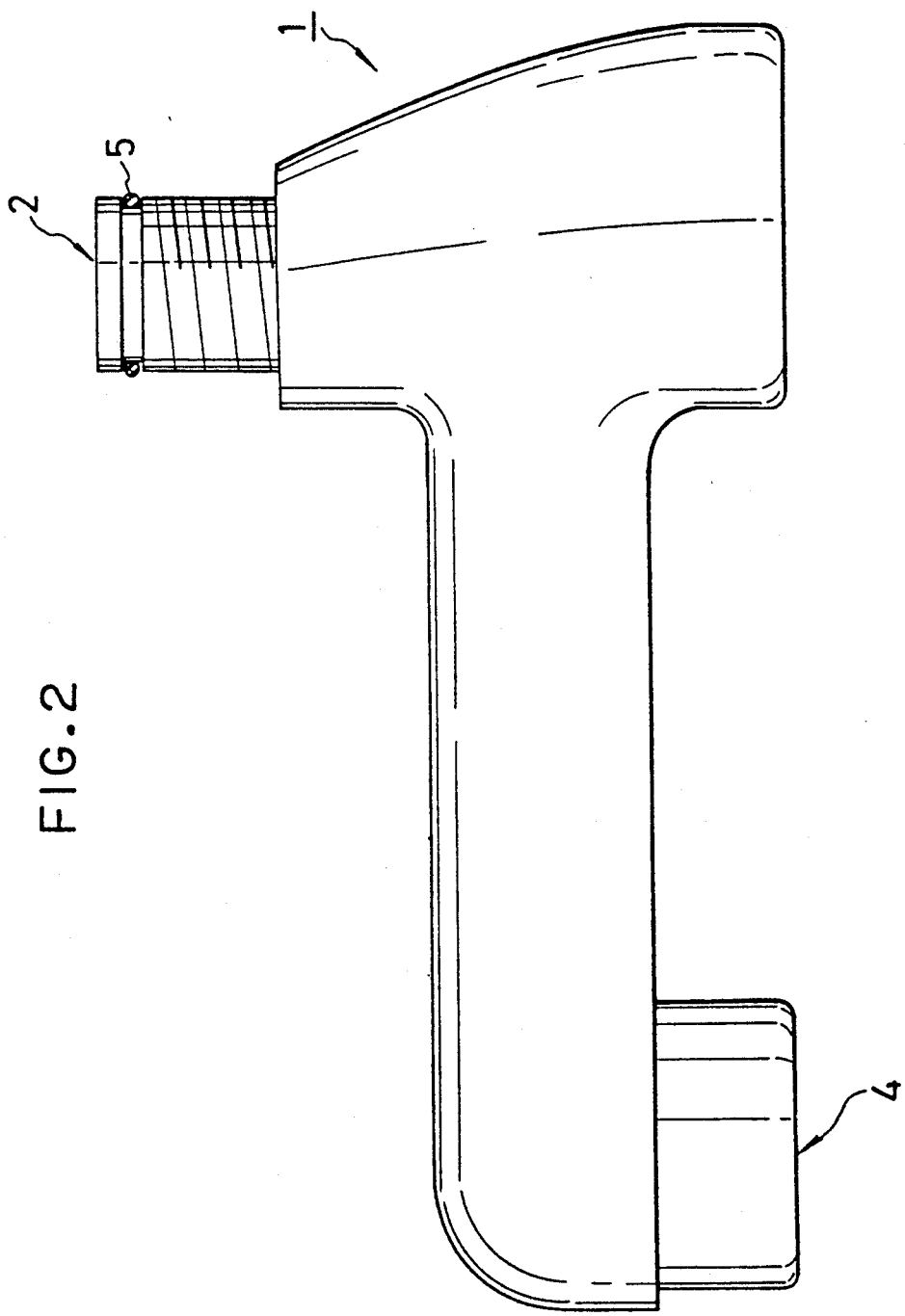
FIG. 2 is a side view of the embodiment.

FIGS. 1 and 2 are sectional and side views of one embodiment of a water faucet. 2 is an inlet port communicated with an outlet port 4 through a discharge passageway 3. A male thread is formed on the outer periphery of the inlet port 2. An O-ring 5 is also fit around the inlet port 2. The water faucet 1 has an integral control chamber 6. Included in the control chamber 6 is a base plate 8 on which a control circuit (not shown) and a LED (light emitting diode) 7 are placed.

A sensor 9 is exposed to the discharge passageway 3 to detect the volume, temperature, pressure, pH (hydrogen ion concentration) or hardness (e.g. calcium carbonate) of water in the discharge passageway 3. As an alternative, the sensor 9 may be disposed behind (or so as not to extend through) the pipe wall of the passageway 3. In such a case, the temperature of water in the passageway 3 can be detected by sensing heat transmitted through the pipe wall.

The sensor 9 is connected to the base plate 8 through a lead wire 10. Two optical fibers 11 and 12 have one ends oriented to face the LED 7. The other ends 11A and 12A of the optical fibers 11 and 12 are positioned to surround the outlet port 4. 13 is an electric cell connected to the base plate 8 through a lead wire 14.

With the water faucet 1 thus constructed, when water temperature detected by the temperature sensor exceeds a predetermined temperature;

when the rate of flow of water detected by the flow sensor exceeds a predetermined rate;

when water pressure exceeds a predetermined pressure;

when pH is deviated from a predetermined range (for example, between 6 and 8); or when water hardness exceeds a predetermined level, LED 7 is turned on to emit color light to water discharged from the outlet port 4. As a result, it can be observed that: the temperature of outlet water exceeds a predetermined temperature; the rate of flow of output water exceeds a predetermined rate; water pressure exceeds a predetermined pressure; ph is deviated from a predetermined range; or hardness exceeds a predetermined level. A user always visually recognize the temperature, the volume, the pressure, pH and hardness of water whenever the water faucet 1 is used.

In the present invention, a water pressure sensor can be used as the sensor 9, and LED is turned on when output water pressure is above a predetermined level. In this way, it can visually be recognized that the pressure of the outlet water from the water faucet 1 is high, and splashing is easily obtainable.

Figure 3:
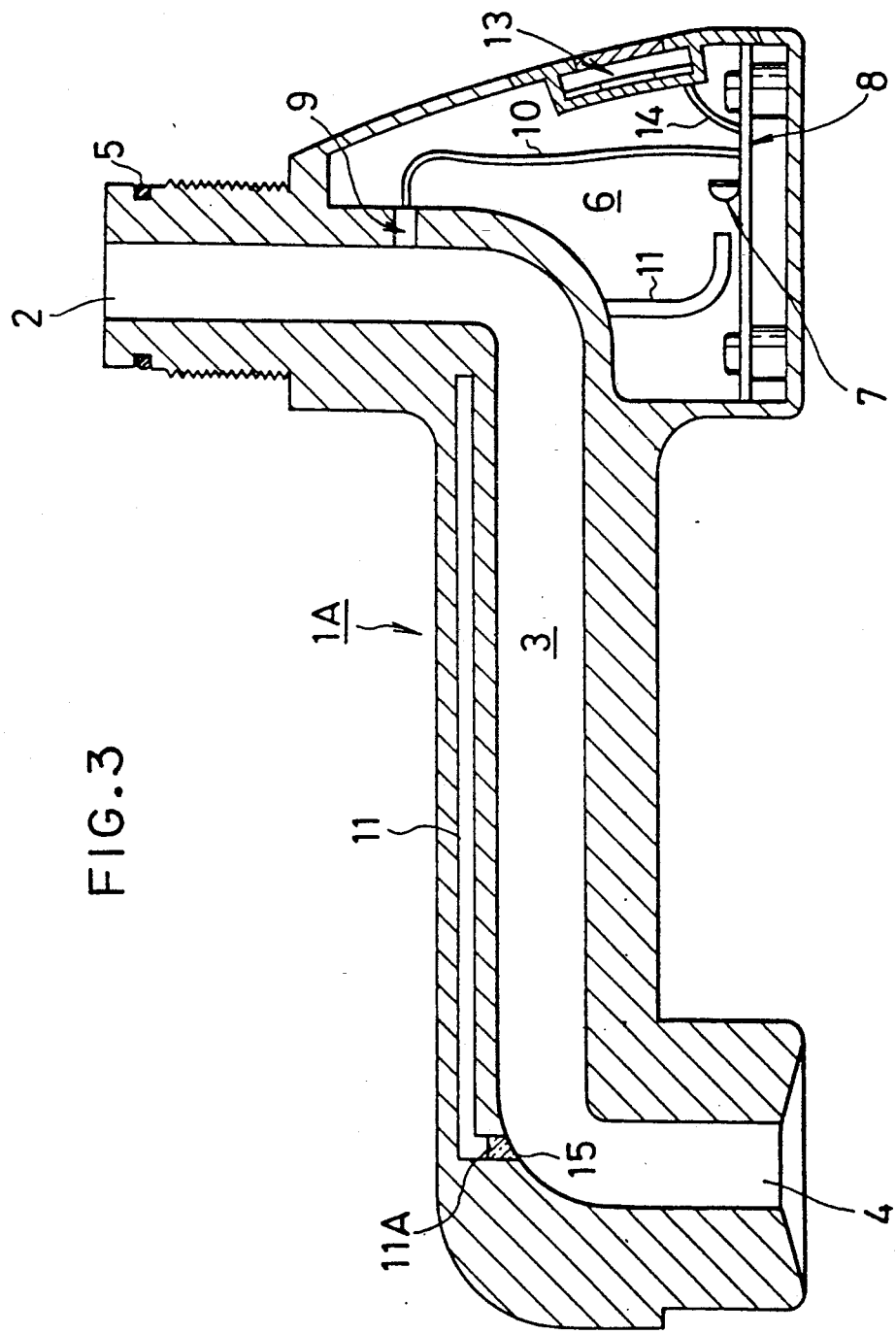
FIGS. 3 and 4 are sectional views of different embodiments.

FIG. 3 is a sectional view of a water faucet 1A according to another embodiment of the present invention. The end 11A of the optical fiber 11 is oriented toward the passageway 3 to emit light to the outlet port 4. 15 is a transparent seal. Now that light is emitted to the output water, this embodiment is also operated in the same manner and provides the same advantages as stated earlier. Preferably, light is emitted from the end 11A of the optical fiber 11 directly to the outlet port 4. Alternatively, light may reaches the outlet port 4 while being normally or randomly reflected from the inner surface of the passageway 3.

Figure 4:
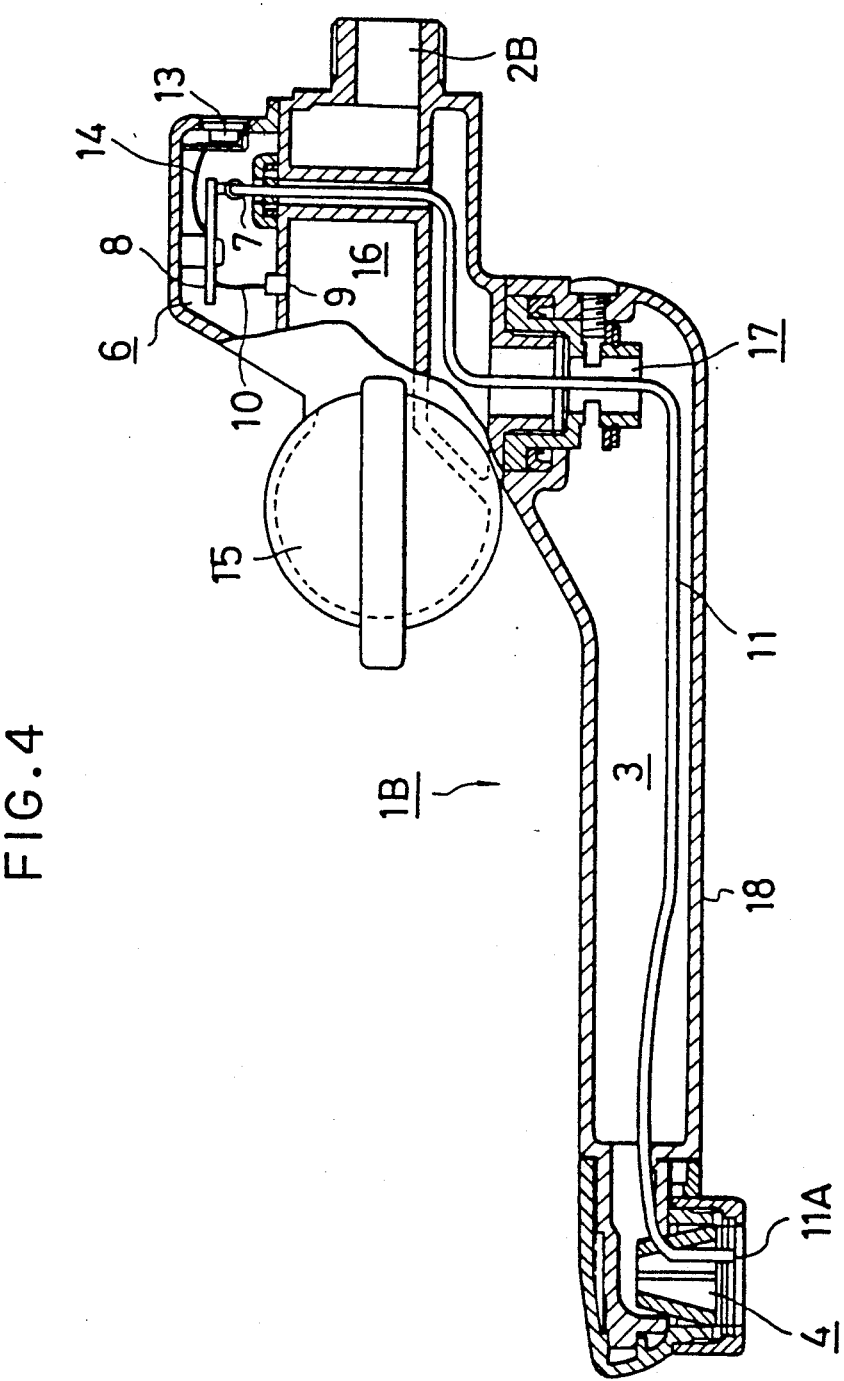

FIG. 4 is a vertical sectional view of a combined hot and cold water faucet 1B. The end 11A of the optical fiber 11 is so oriented as to emit light to the outlet port 4.

Hot water flows into a mixing valve 15 through an inlet port 2A (not shown). Cold water flows into the mixing valve 15 through an inlet port 2B. The mixing valve 15 is operable to mix hot and cold water in a manner to produce a mixture of a predetermined temperature. The mixture then flows into a mixing chamber 16 and out of the outlet port 4 through an outlet opening 17 and a conduit 18. The other like reference numerals in FIG. 4 designate like elements in FIG. 1. Now that light is emitted to the output water, this embodiment is also operable in the same manner and provides the same advantages as stated earlier.

Figure 5:
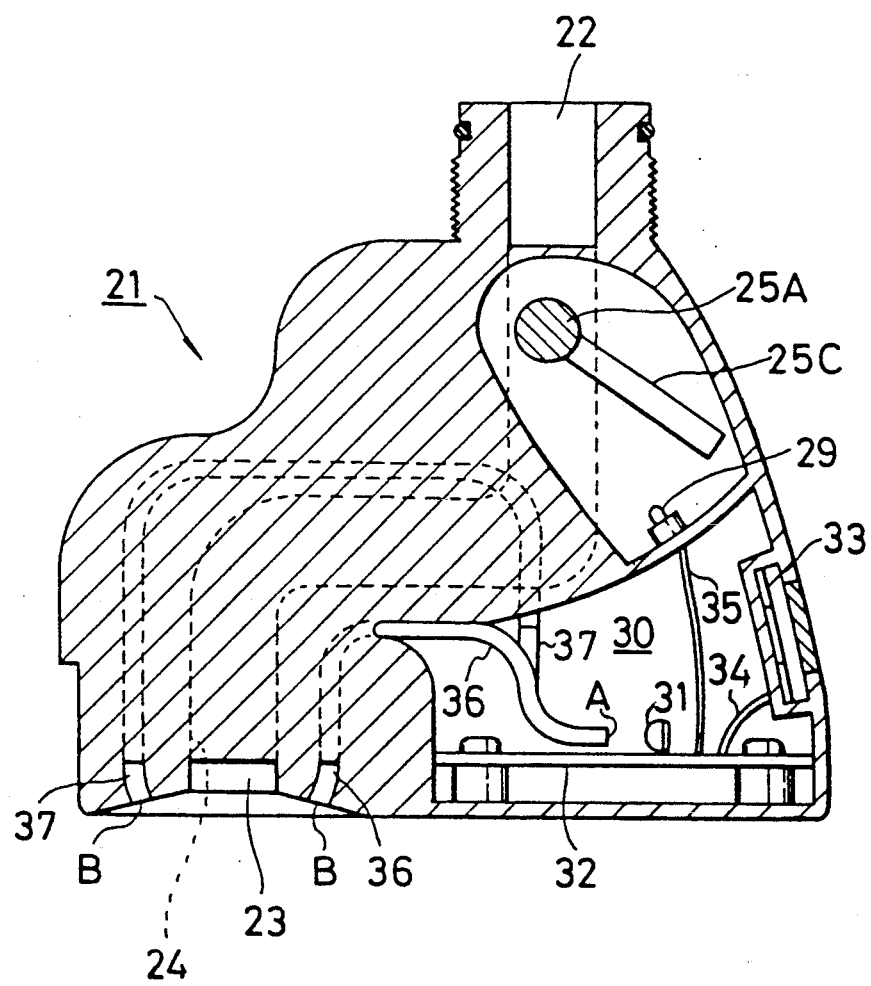
FIG. 5 is a vertical sectional view of a water purifier according to one embodiment of the present invention.
Figure 6:
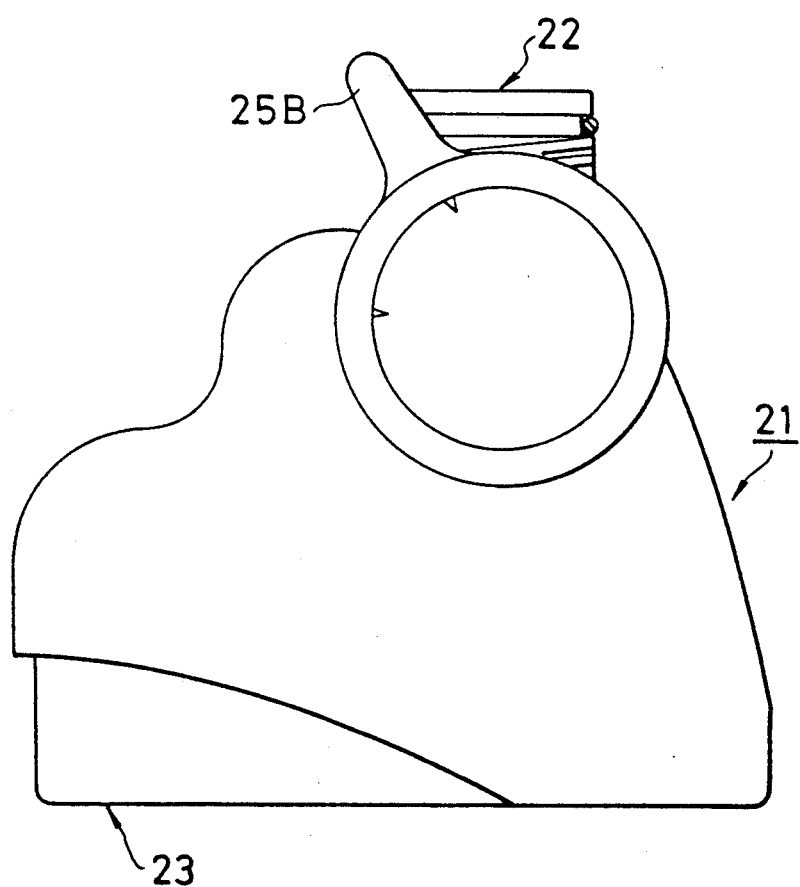
FIG. 6 is a side view of the water purifier.
Figure 7:
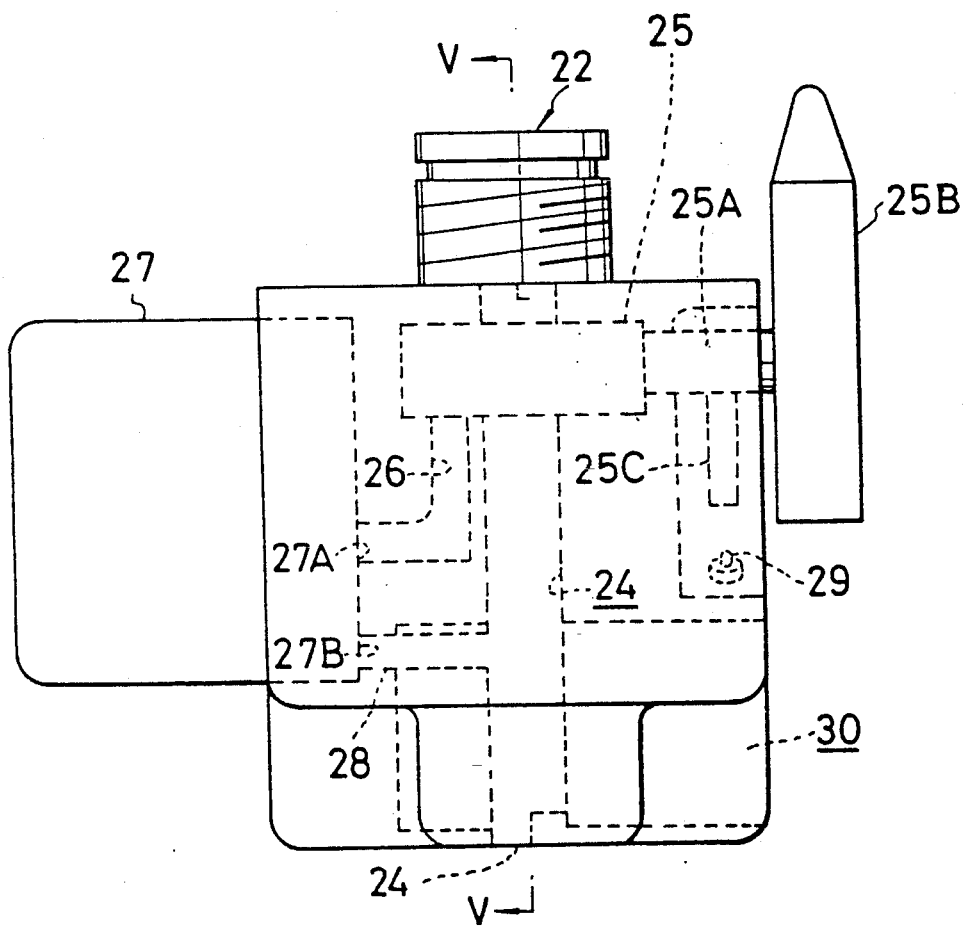
FIG. 7 is a front view of the water purifier.

FIG. 5 is a vertical sectional view of an apparatus for discharging water (water purifier) according to one embodiment of the present invention (taken along the line V—V of FIG. 7). FIG. 6 is a side view, and FIG. 7 is a front view.

A water purifier 21 includes an inlet port 22 at its upper portion and an outlet port 23 at its lower portion. The inlet port 22 and the outlet port 23 are communicated with one another through a passageway 24. A changeover valve 25 is arranged in the passageway 24 to selectively communicate the inlet port 22 with the outlet port 23 and a branch passage 26. The branch passage 26 is coupled to an inlet 27A of a purifier cartridge 27. The purifier cartridge 27 has an outlet 27B communicated with the passageway 24 through a purified water passage 28.

The changeover valve 25 has an operating shaft 25A extending externally of the water purifier 21. A handle 25B is secured to one end of the operating shaft 25A. An arm 25C extends radially from the operating shaft 25A. When the handle 25B is operated, the arm 25C is brought into engagement with a limit switch 29. A control chamber 30 is defined at the rear of the water purifier 21 and includes a circuit board 32 on which a control circuit (not shown) and LED 31 are placed. 33 is an electric cell adapted to supply electric power to the circuit board 33. The electric cell 33 and the limit swicth 29 are connected to the circuit board 32 through lead wires 34 and 35, respectively.

Two optical fibers 36 and 37 have one ends A oriented to receive light from LED 31. The other ends B of the optical fibers 36 and 37 are positioned around the outlet port 23 so as to direct light from LED 31 to water flowing out of the outlet port 23.

With the water purifier 21 thus constructed, when the handle 25B is turned to a tap water position, the changeover valve 25 is operable to provide a direct communication between the inlet port 22 and the outlet port 23. Tap water flows from the inlet port 22 toward the outlet port 23 through the passageway 24, not through the purifier cartridge 27. The tap water is then discharged from the outlet port 23. In this case, LED 31 is rendered inoperative, and no light is directed to tap water flowing out of the outlet port 23.

When the handle 25B is turned to a purified water position, the inlet port 22 is brought into communication only with the branch passage 26. Tap water flows from the inlet port 22 into the purified water cartridge 27. The tap water is, then, purified by a purifying agent such as an activated carbon filled in the purified water cartridge 27. This purified water is returned to the passageway 27 through the purified water passage 28 and then, discharged from the outlet port 23. When the handle 25B is turned to its purified water position, the arm 25C comes into contact with the limit switch 29. A signal is then send to the circuit on the circuit board 32. A control circuit on the circuit board 32 is rendered operative to turn on LED 31 in response to the input signal. Light is emitted from the end A of LED 31 to the optical fibers 36 and 37. The light is, then, emitted from the other end B of the optical fibers 36 and 37 to purified water flowing out of the outlet port 23.

LED 31 emits color light. Accordingly, the output purified water is observed as if it is colored. A user almost always views water discharged from the outlet port 23 when the water purifier 21 is in use. The user can visually recognize whether the output water is purified by looking at the water to which color light is emitted.

Figure 8:
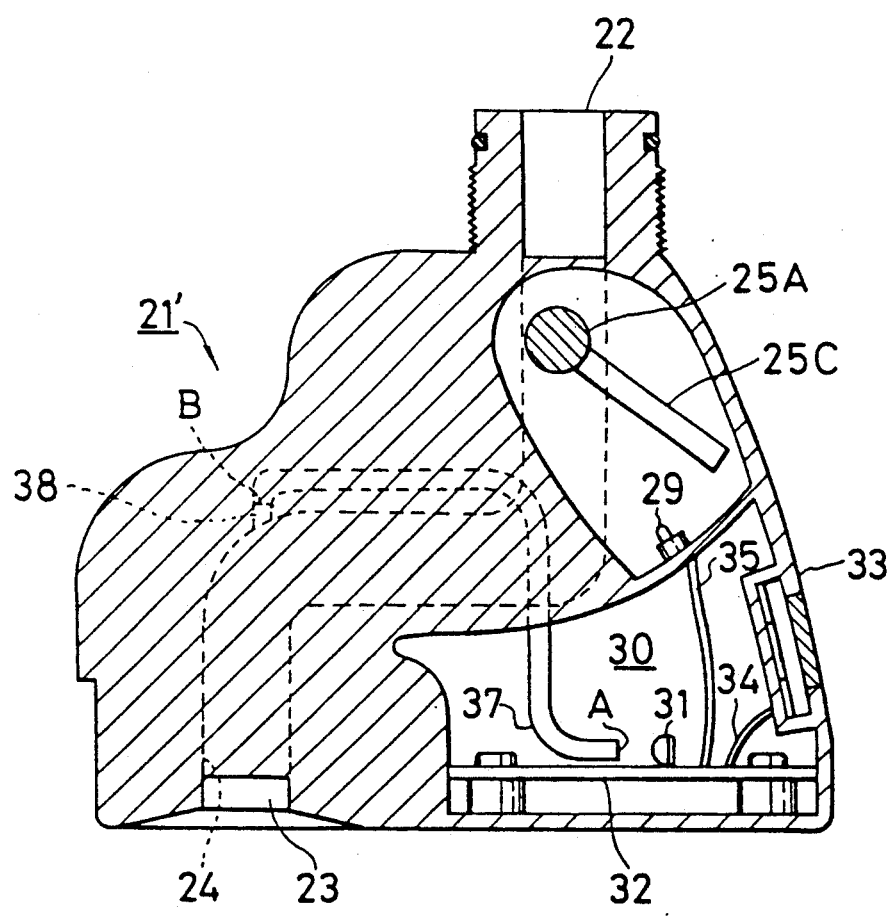
FIGS. 8 and 9 are front views of water purifier according to different embodiments of the present invention.

FIG. 8 illustrates a water purifier 21' according to another embodiment of the present invention. The end B of the optical fiber 37 is oriented toward the passageway 24 so as to emit light to the outlet port 23. 38 is a transparent seal. Now that light is emitted to the outlet port 23, this embodiment is also operated in the same manner and provides the same advantages as stated earlier.

Preferably, light is emitted from the end B of the optical fiber 37 directly to the outlet port 23. Alternatively, light may reach the outlet port 23 while being normally or randomly reflected from the inner surface of the passageway 24.

Figure 9:
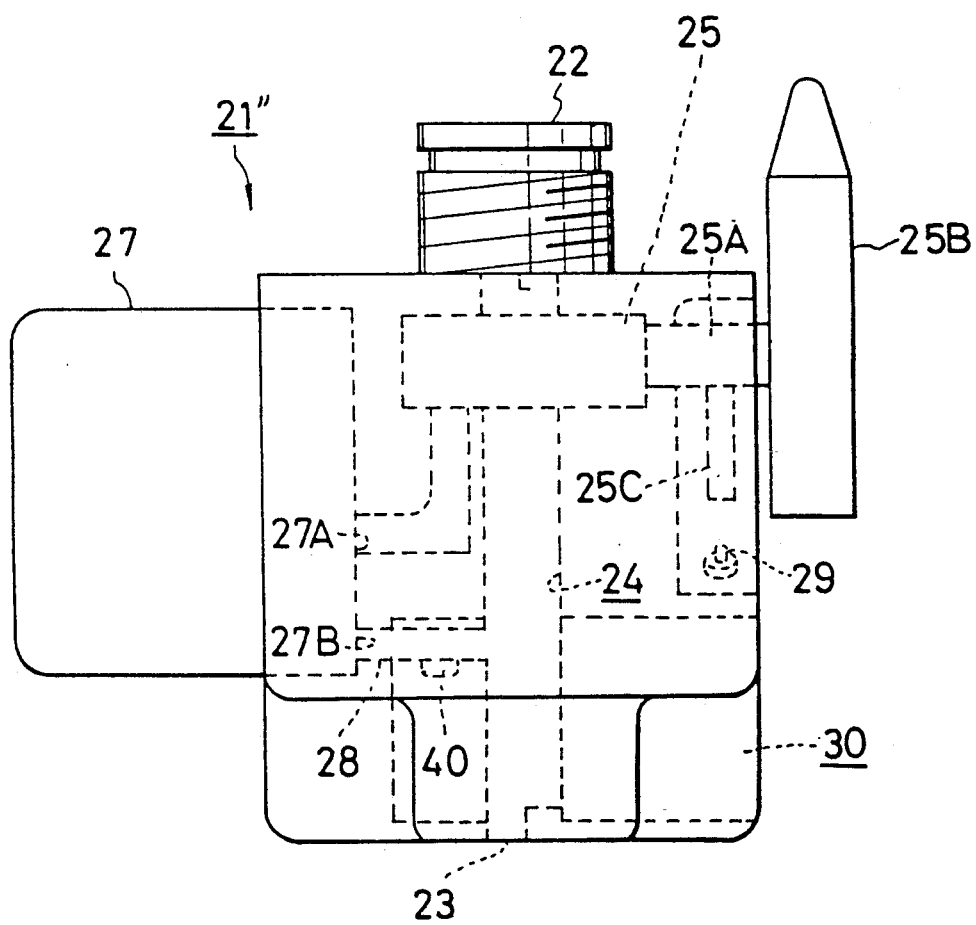

FIG. 9 is a front view of a water purifier 21" according to a still another embodiment of the present invention. In this embodiment, a water quality sensor 40 is arranged in the purified water passage 28 to detect the quality of purified water. This sensor 40 is operable to send a signal to the circuit board (not shown in FIG. 5). In this embodiment, LED (not shown) is rendered operative to emit light of different color to water discharged from the outlet port 23 when the quality of the water as purified in the purified water cartridge 27 is below a predetermined level. Thus, the user can recognize whether the service life of the purifying agent in the purified water cartridge 27 is over.

The water quality sensor 40 may be in the form of an electric conductance meter or chlorine sensor.

In the embodiment of the present invention, as shown in FIG. 9, a flowmeter (not shown) may be provided in place of the water purified sensor 40. In the circuit board 32, the flow of purified water flowing through the purified water passage 28 is calculated. Light of different color is then emitted to the water discharged from the outlet port 23 when the total amount of flow is above a predetermined level. In this way, the user is able to know the time to replace the existing purifying agent.

Figure 10:
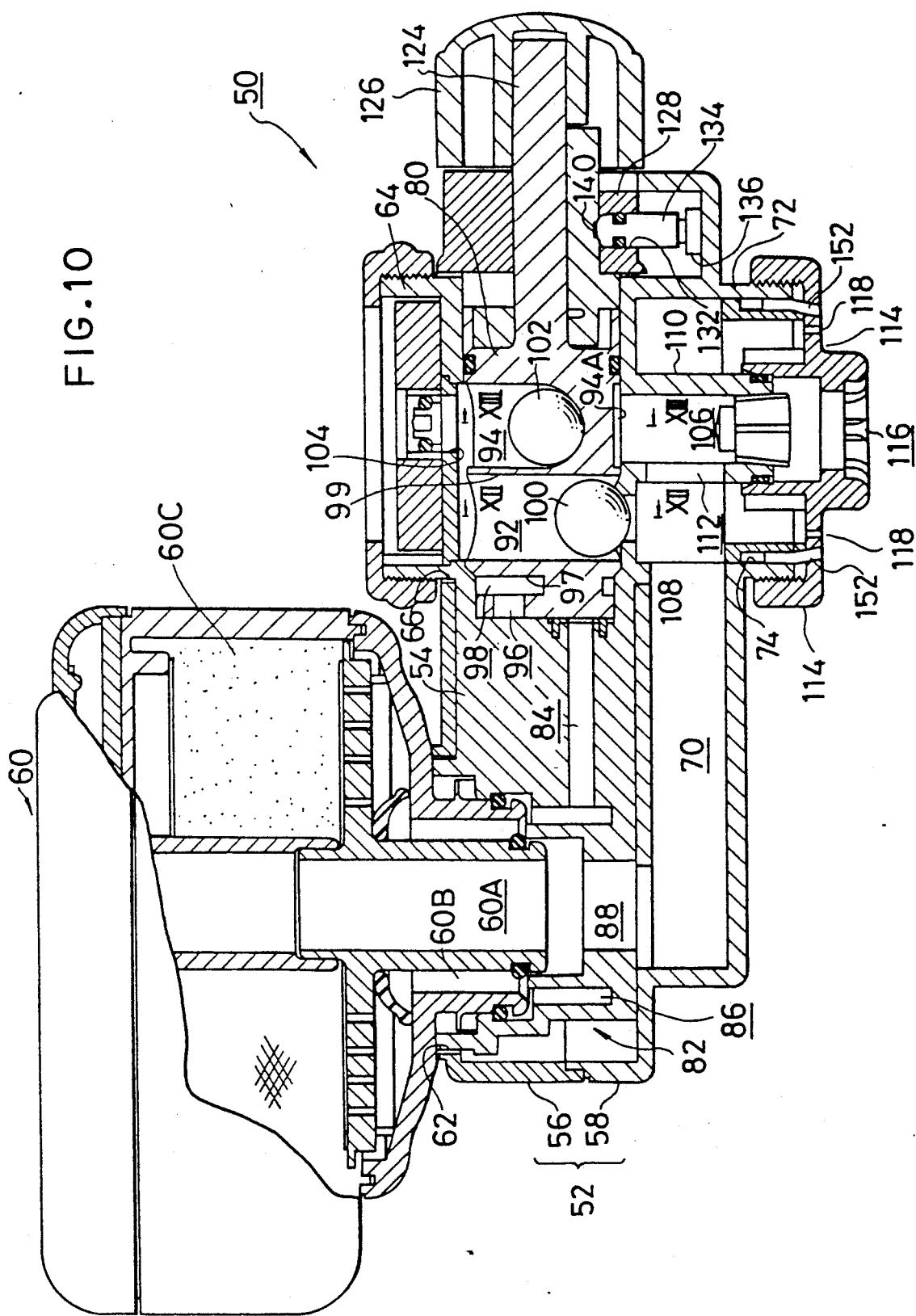
FIG. 10 is a vertical sectional view of a water purifier according to one embodiment of the present invention.
Figure 11:
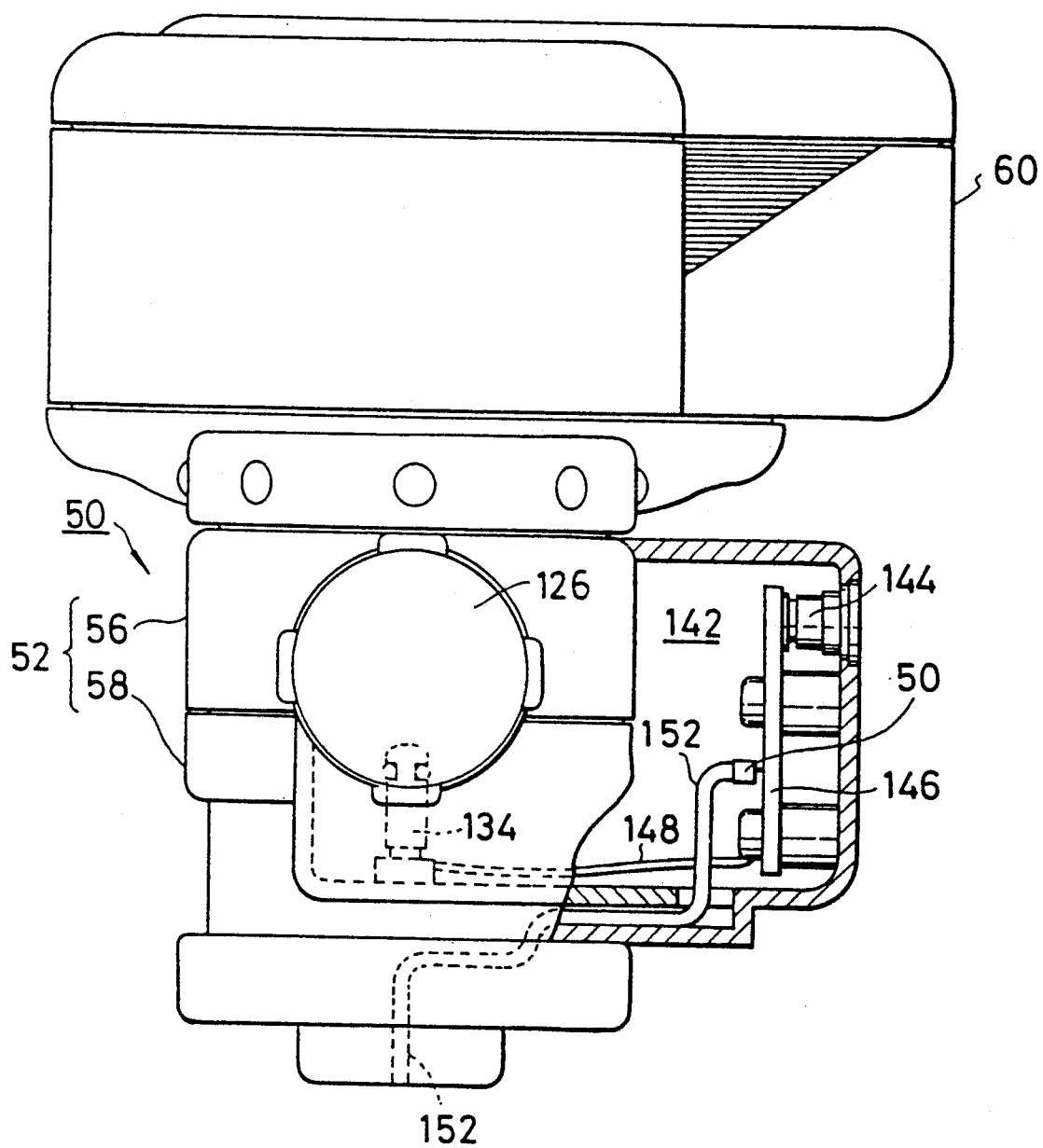
FIG. 11 is a right side view of the water purifier.
Figure 12:
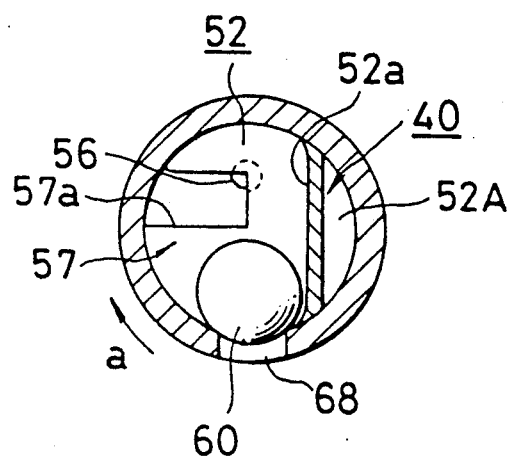
FIGS. 12 and 13 are sectional views showing the principal part of a water faucet.
Figure 13:
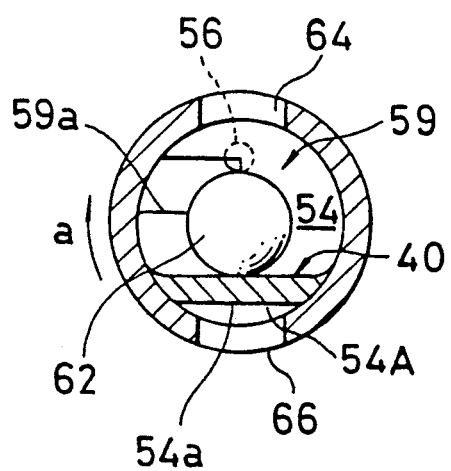
Figure 14:
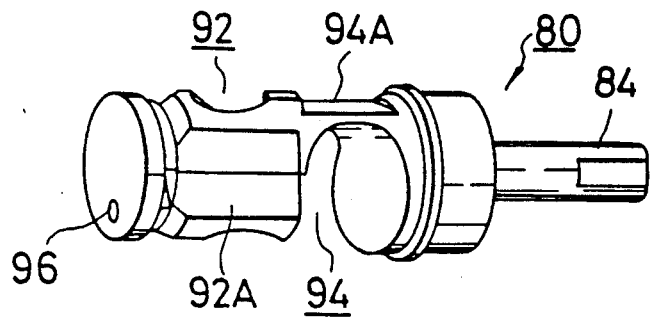
FIGS. 14, 15 and 16 are perspective views of a valve body 80.
Figure 15:
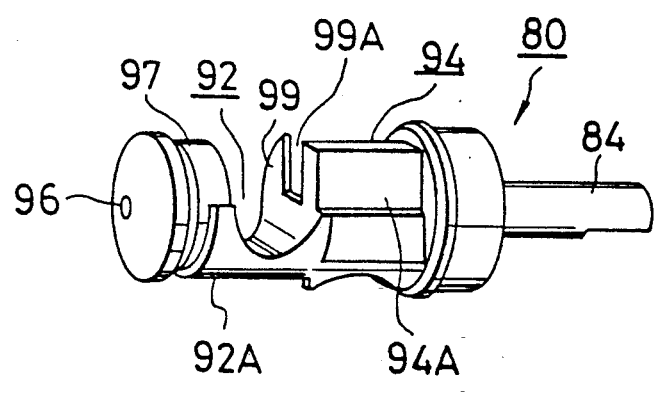
Figure 16:
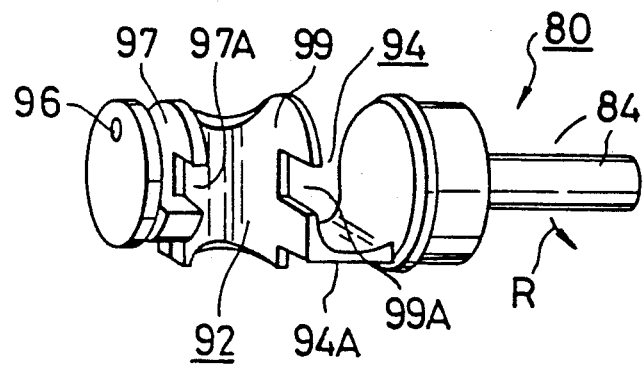

FIG. 10 is a vertical sectional view of a water faucet 50 for use in the water purifier according to one embodiment of the present invention. FIG. 11 is a right side view, partly in section, of the water faucet. FIGS. 12 and 13 are sectional views of a valve casing taken along the lines of XII—XII and XIII—XIII of FIG. 10. FIGS. 14, 15 and 16 are perspective views of a valve element 80.

The water faucet 50 includes a faucet casing 52 in which a valve body 54 is received. The faucet casing 52 includes an upper casing 56 and a lower casing 58. The upper casing 56 is flat as viewed in plan. An opening 62 is formed in one side of the top of the upper casing to mount a purified water cartridge 60. Formed in the opposite side of the top of the upper casing is an opening 66 through which an inlet port 64 of the rotary valve 54 extends outwardly of the casing 52.

The lower casing 58 is also flat as viewed in plan and has an opening 74 through which an outlet port 72 of the valve body 54 extends outwardly of the faucet casing 52.

A passage 70 is defined in the bottom of the lower casing 58 so that water as purified in the purified water cartridge 60 flows into the outlet port 72.

A valve element 80 is inserted into the valve body 54. The valve body 54 has an integral purified water cartridge connecting section 82. Water flows from the valve element 80 into the purified water cartridge connecting section 82 through a connecting passage 84. The purified water cartridge connecting section 82 includes an outer passage 86 and an inner passage 88.

A purified water outlet 60A extends centrally from the bottom of the purified water cartridge 60. A unpurified water inlet 60B is defined coaxially around the purified water outlet 60A. The purified water cartridge 60 includes a filtering element 60C such as an activated carbon.

Water flows from the outer passage 86 into the purified water cartridge 60 through the unpurified water inlet 60B and is, then, purified by means of the element 60C. The water thus purified flows from the purified water outlet 60A to the inner passage 88.

The valve element 80 is substantially cylindrical and includes a first ball holding recess 92 and a second ball holding recess 94.

As clearly shown in FIGS. 14, 15 and 16, the ball holding recess 92 extends laterally of the valve element 80. This ball holding recess 92 is communicated with an end opening 96 of the valve element 80 through a slot or passage 98. A ball 100 is received in the ball holding recess 92.

The ball holding recess 94 extends laterally of the valve element 80. The ball holding recess 94 extends at right angles to the ball holding recess 92. A ball 102 is received in the ball holding recess 94.

A partition 97 extends between the ball holding recess 92 and the passage 98 and has a notch 97A. A partition 99 extends between the ball holding recess 92 and the ball holding recess 94 and has a notch 99A. The slot or passage 98, the ball holding recess 92 and the ball holding recess 94 are mutually communicated with one another through these notches 97A and 99A. Formed behind the ball holding recesses 92 and 94 are arcuate recesses 92A and 94A.

The valve body 54 includes an inlet port 104 at its top, and outlet ports 106 and 108 at its bottom.

A tubular member 110 extends downwardly from the valve body 54 and forms an outlet port 106. An opening 112 is defined in the tubular member 110 to provide a communication between the passage 70 and the interior of the tubular member 110.

The reference numeral 114 denotes a cap. The cap 114 has a central outlet 116 in communication with the outlet port 106.

Shower outlets 118 are defined in the periphery of the cap 114 and communicated with the outlet port 108.

The shower outlets 108 are also communicated with the passage 70.

An operating shaft 124 extends from one end of the valve element 80 opposite to the end in which the end opening 96 is defined. A handle 126 is fit over the operating shaft 124. The operating shaft 124 extends through the faucet casing 52.

The reference numeral 128 denotes a bearing for the operating shaft 124. The bearing 128 has a radial bore 132 into which a switch 134 extends. The switch 134 includes a spring adapted to urge a protrusion 136 outwardly. The protrusion 136 is in contact with the inner surface of the lower casing 58.

A recess 140 is formed in the outer periphery of the operating shaft 124. When the head of the switch 134 extends into the recess 140, the switch 124 is extended under the influence of the internal spring so as to open the contact of the switch 124. On the other hand, when the head of the switch 134 comes into contact with the outer periphery of the operating shaft other than the recess 140, the switch 134 is shortened to close the contact of the switch.

Formed behind the casing 52 is a circuit chamber 142 in which an electric cell 144, a circuit board 146 and LED 150 are situated. An optical fiber 152 is positioned to direct light from LED 150 to near the outlet 118. 148 is a lead wire by which the switch 134 and the board 146 are connected together.

The water purifier includes the water faucet 50 and the purified water cartridge 60. With this arrangement, water flows from the inlet port 104 into the valve element whereby the water separately flows.

As shown in FIGS. 10 and 16, if the valve element 80 is positioned such that the first ball holding recess 92 is oriented toward the inlet port 104 and the outlet port 108, and the second ball holding recess 94 is oriented only toward the inlet port 104, then the end opening 96 is disconnected from the connecting passage 84, and the shower outlets 108 are closed by the ball 100. Water, as introduced through the inlet port 104, flows around the valve element 80, through the recess 94A and the tap water outlet port 106, and out of the central outlet 116.

If the valve element 80 is rotated by 90° in the direction of the arrow R in FIG. 16 from the position shown in FIGS. 10 and 16 to the position shown in FIG. 15, then the outlet port 108 is opened. Instead, the tap water outlet port 106 is closed by the ball 102. The connecting passage 84 remains closed. As a result, water, introduced through the inlet port 104, flows around the valve element 80, through the outlet port 108 and out of the shower outlets 118.

If the valve element 80 is rotated by 180° from the postion shown in FIG. 16 to the position shown in FIG. 14, then the ball holding recess 92 is oriented toward the outlet port 108. This causes the ball 100 to close outlet port 108. The ball holding recess 108 is also oriented toward the tap water outlet port 106. This causes the ball 102 to close the tap water outlet port 106. The end opening 96 is instead brought into communication with the connecting passage 84. As a result, water from the inlet port 104 flows, through the passage 98, the end opening 96, the connecting passage 84, the outer passage 86, the faucet casing 60, the inner passage 88 and the passage 70 in that order, and out both of the central outlet 116 and the shower outlets 118.

When the valve element is rotated to the position shown in FIG. 14, the outer periphery of the operating shaft 124, except for the recess, comes into contact with the switch 134. This results in a decrease in the length of the switch 134. The switch is then on so that LED 150 may emit light. The light is emitted from LED 150 through the optical fiber 152 to the output water. Now that color light is directed to the output water, it is easily seen whether the output water has been purified in the purified water cartridge 60.

INDUSTRIAL APPLICABILITY

As discussed above, according to the present invention, a user can safely visually recognize the temperature, volume, pressure, concentration (for example, pH, and hardness), and kinds of water (for example, purified water and tap water). In the present invention, it may, for example, emit light of different colors to the output water in response to water temperature. Light may be used to illuminate rooms. Additionally, light may be emitted when the temperature or volume of water is increased. Light colors or intervals of emission may be selected to prevent burning of the user or to save on water.

I claim:

1. An apparatus for discharging water comprising,
a water outlet device having a water passageway therein and an outlet communicating with the passageway for ejecting water,
sensor means for sensing characteristics of water flowing through the water passageway, and
light emitting means associated with the sensor means and having a light emitting device, an optical fiber for guiding light from the light emitting device and a light emitting portion located inside the water outlet device, said light emitting portion being situated adjacent to the water passageway near the outlet to orient toward the outlet through a part of the water passageway so that when light is emitted through the light emitting portion, light passes through water flowing through the water passageway and is seen outside the outlet.

2. An apparatus for discharging water as claimed in claim 1, wherein said light emitting device is a light emitting diode.

3. An apparatus for discharging water as claimed in claim 1, wherein water ejected from the outlet has a columnar shape without spreading outwardly from the outlet.

4. An apparatus for discharging water as claimed in claim 1, wherein said water outlet device is a faucet.

5. An apparatus for discharging water comprising,
a water outlet device having a water passageway therein and an outlet communicating with the passageway for ejecting water,
sensor means for sensing characteristics of water flowing through the water passageway, and
light emitting means associated with the sensor means and having a light emitting device, an optical fiber for guiding light from the light emitting device and a light emitting portion located inside the outlet of the water outlet device without extending outwardly from the water outlet device, said light emitting portion being oriented outwardly along the water passageway so that when light is emitted through the light emitting portion, light is directly ejected into water and is seen outside the outlet.

6. An apparatus for discharging water as claimed in claim 5, wherein said light emitting device is a light emitting diode.

7. An apparatus for discharging water as claimed in claim 5, wherein water ejected from the outlet has a columnar shape without spreading outwardly from the outlet.

8. An apparatus for discharging water comprising, a water outlet device having a water passageway therein and an outlet communicating with the passageway for ejecting water in a form of water column, sensor means for sensing characteristics of water flowing through the water passageway, and light emitting means associated with the sensor means and having a light emitting device, optical fibers for guiding light from the light emitting device and a plurality of light emitting portions located inside the water outlet device to surround the outlet, said light emitting portions being directed toward water ejected from the outlet so that when light is emitted from the light emitting portions, light hits water ejected from the outlet and is seen outside the outlet.

9. An apparatus for discharging water as claimed in claim 8, wherein said light emitting device is a light emitting diode.

10. An apparatus for discharging water comprising, a water outlet device having a water passageway therein and a plurality of outlets communicating with the water passageway for ejecting and spreading water in a form of shower, sensor means for sensing characteristics of water flowing through the water passageway, and light emitting means associated with the sensor means and having a light emitting device, optical fibers for guiding light from the light emitting device and a plurality of light emitting portions located inside the water outlet device to surround all the outlets, said light emitting portions being directed toward water ejected from the outlets so that when light is emitted from the light emitting portions, light hits water ejected from the outlets and is seen outside the outlets.

11. An apparatus for discharging water as claimed in claim 10, wherein said light emitting device is a light emitting diode.

12. An apparatus for discharging water comprising, a water outlet device having a plurality of water passageways therein, passage selection means for selecting one of the water passageways, and an outlet communicating with the passageways for ejecting water, sensor means for sensing characteristics of water flowing through the water passageways and communicating with the passage selection means, and light emitting means associated with the sensor means, said sensor means showing a condition of the passage selection means at the light emitting means, said light emitting means having a light emitting portion located inside the water outlet device, said light emitting portion being situated adjacent to the water passageway near the outlet to orient toward the outlet through a part of the water passageway so that when light is emitted through the light emitting portion, light passes through water flowing through the water passageway and is seen outside the outlet.

13. An apparatus for discharging water as claimed in claim 12, further comprising a filtering element disposed in one of said feed water passageways.

14. An apparatus for discharging water comprising, a water outlet device having a water passageway therein and an outlet communicating with the passageway for ejecting water, sensor means for sensing characteristics of water flowing through the water passageway, said characteristics sensed being water concentration of at least one of pH and hardness, and light emitting means associated with the sensor means and having a light emitting portion located inside the water outlet device, said light emitting portion being situated adjacent to the water passageway near the outlet to orient toward the outlet through a part of the water passageway so that when light is emitted through the light emitting portion, light passes through water flowing through the water passageway and is seen outside the outlet.

* * * * *